United States Patent
Parng et al.

(10) Patent No.: US 7,588,727 B2
(45) Date of Patent: Sep. 15, 2009

(54) MICROFLUIDIC CHIP

(75) Inventors: Shaw-Hwa Parng, Hsinchu (TW);
Tung-Ming Yu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 768 days.

(21) Appl. No.: 11/151,443

(22) Filed: Jun. 14, 2005

(65) Prior Publication Data

US 2006/0188403 A1    Aug. 24, 2006

(30) Foreign Application Priority Data

Feb. 18, 2005    (TW) ............................... 94104888 A (51) Int. Cl.
*B01L 3/00*    (2006.01)
*C12Q 1/68*    (2006.01)
*G01N 25/00*    (2006.01)
*G01N 25/20*    (2006.01)
*G01N 25/18*    (2006.01)

(52) U.S. Cl. .................... 422/99; 422/50; 422/82.12; 422/98; 436/147; 436/149

(58) Field of Classification Search .......... 422/50, 422/82.12, 98, 99; 436/147, 149
See application file for complete search history.

(56) References Cited

OTHER PUBLICATIONS

Sun, Kai et al., "A Heater-Integrated Transparent Microchannel Chip for Continuous-Flow PCR", Sensor and Actuators B 84 (2002) 283-289.
Schabmueller, C. G. J. et al., "Integrated diode detector and optical fibres for in situ detection within micromachined polymerase chain reaction chips" Journal of Micromechanics and Microengineering, (2001) 329-333.
Bu, Minqiang et al., "Design and theoretical evaluation of a novel microfluidic device to be used for PCR", Journal of Micromechanics and Microengineering, 2003, S125-S130.
Lagally Eric T. et al., "Fully integrated PCR-capillary electrophoresis microsystem for DNA analysis", The Royal Society of Chemistry, Lab on a Chip, 2001, 1, 102-107.
Kopp, Martin U. et al., "Chemical Amplification: Continuous-Flow PCR on a Chip", Science; May 15, 1998, 280,5366, ProQuest Science Journals, p. 1046.
Lee, Dae-Sik et al., "Bulk-micromachined submicroliter-volume PCR chip with very rapid thermal response and low power consumption", Miniaturisation for Chemistry, Biology & Bioengineering, Royal Society of Chemistry 2004, Lab Chip, 2004, 4, 401-407.

*Primary Examiner*—Jill Warden
*Assistant Examiner*—Dean Kwak
(74) *Attorney, Agent, or Firm*—Birch, Stewart, Kolasch & Birch, LLP (57) ABSTRACT

A microfluidic chip on a transparent substrate includes microchannels, and an electric layer having a heater and a sensor layout on the microchannel nearby and aside for supplying heat source and sensing the temperature individually. The sensor is close to the microchannel for controlling the temperature accurately. Hence, the microfluidic chip can measure the temperature precisely without using an isolation layer and lower energy consumptions and reduce production costs.

19 Claims, 6 Drawing Sheets

MICROFLUIDIC CHIP

BACKGROUND

1. Field of the Invention

The invention relates to a microfluidic chip, which is utilized in a poly-enzyme chain reaction and hybrid array of biochemical experiments, and in particular to a microfluidic chip, which can be utilized to raise the efficiency of biochemical reactions.

2. Related Art

The poly-enzyme chain reaction is presently the most frequently used method for nucleotide multiplication and augmentation. The quantity of DNA (deoxyribonucleic acid) can be multiplied exponentially several million times through the repeated denatured, annealing and extension processes of the segments of DNA, by thermal circulation, so that the traditional time consuming process of bio-medical sample body treatment and its reaction schedule can be shortened significantly.

In the poly-enzyme chain reaction, the sample body must be augmented through a micro channel-electrode-on-chip device having electrodes and micro-channel disposed thereon, to speed up and facilitate the subsequent tests and examinations. To achieve this purpose, the microfluidic chip must fulfill the following requirements:

(1) it must be stably bonded and heat resistant against high temperature;

(2) it must be transparent to light to enable the observation by an optical system; and (3) it must be conveniently connected to the subsequent biochemical reactions.

In general, the microfluidic chip is made of a chip bonding the micro-channel, and an electrode layer made of metal, and the bonding method utilized usually can be classified into the following three categories:

1. The anodic bonding: etching a microstructure on a silicon substrate: next, bonding the anode to a glass substrate having electrodes; then, bonding the two substrates together through high voltage and high temperature (approximately, 1000V and 400° C. respectively). The bonded glass substrate and silicon substrate thus produced has the characteristics of single side transmittance of light, however, the equipment required to use in this process is quite expensive, thus raising the production cost.

2. The chemical bonding; selecting the adhesive material suitable for use as a substrate interface; bonding the two substrates together through bonding the chemical bonds on the surface of the substrates. In this bonding method, different adhesive material is selected for bonding the substrates of different materials. However, the quality of the chip thus produced is not quite satisfactory, since the adhesive material is liable to block the micro-channel in the substrate. Besides, the bonding strength at high temperature is not sufficient enough.

3. The thermal fusion bonding: bonding two substrates together by heating the two substrates to the point of getting soft. The advantage of this method is that good bonding strength can be achieved between the two substrates, and the optical characteristics of the substrates are not affected after the bonding. However, it suffers from the drawbacks that quite a few materials are not suitable for use in the high temperature environment as required by this method.

As to the classification of the microfluidic chip, it can be classified as fixed type heating and movable type heating depending on the manner of heating the test fluid. The main feature of the fixed type heating is that the test fluid is stationary and does not flow during the cooling or heating process. The temperature variations are controlled by the feedback of the temperature sensor to regulate the electric power used for heating, while in the moving type heating, the test fluid is made to flow to the various positions of the chip to achieve heating or cooling, and the heater is used to provide heat to achieve a fixed temperature at the various positions of the chip, and the temperature variations of the chip are obtained and controlled by driving the test fluid to the various positions of the chip by the outside force. In addition to the above-mentioned fixed type heating and moving type heating method, there is another non-contact type heating method, wherein the rise and fall of the temperature is achieved and controlled by heating the test fluid with the infrared light radiation and detecting the temperature variation by the sensor.

Besides, the microchannel-electrode-on-chip structure may be further classified as a single-faced type and a double-faced type depending on the disposition position of the electrode. The electrode is provided with a heater wire and a sensor wire. Ideally, the heater wire and the sensor wire are arranged as close to the test fluid in the microchannel as possible, as such to obtain the optimum heat conduction efficiency and actual temperature variations. However, in practice, due to restrictions of the manufacturing process and the temperature controlled environment, if the test fluid is allowed to directly contact the electrode, it is liable to cause the hydrolysis of the electrode, and its temperature control effect is not so good. To avoid the electrode being directly exposed to the test fluid, in the prior art, the method adopted is through utilizing the insulation layer and arranging the wirings of the electrode on the backside of the insulation layer or arranging the electrode in different layers. However, by doing so, the production cost will be raised significantly. In addition, the distance between the heater wire and the sensor wire will affect the temperature variation of the test fluid. If the sensor wire is arranged too close to the heater wire, then the temperature sensed by the sensor wire is the temperature variation of the heat source but not the temperature variation of the test fluid. On the contrary, if the sensor wire is arranged too far away from the heater wire, then the loss of heat energy is raised and the sensitivity of the temperature measurement is decreased. The details of the above-mentioned effects will be discussed more thoroughly as follows, in conjunction with the related drawings.

Figure 1A:
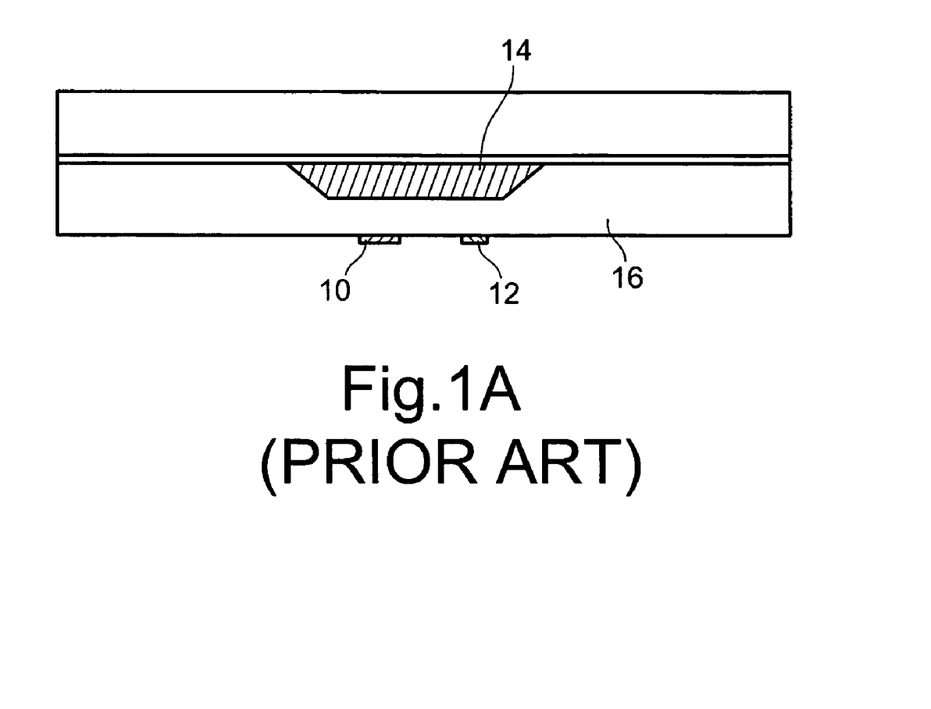
FIGS. 1A & 1B are the schematic diagrams illustrating the cross sections of the microfluidic chips of the prior art.
Figure 1B:
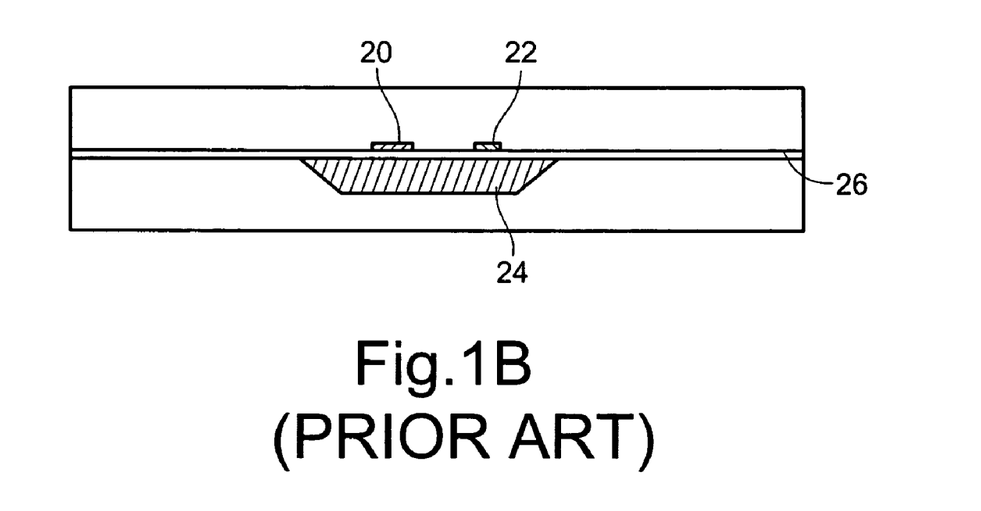

Refer to FIGS. 1A & 1B for the schematic diagrams illustrating the cross sections of two kinds of the microfluidic chips used in the prior art. As shown in FIG. 1A, the first arrangement utilized is to arrange the heater wire 10 and the sensor wire 12 on the backside of the microchannel 14 so that the heat conduction is done through the substrate 16. As such, the efficiency of heat conduction is reduced enormously, thus it is not easy to effectively heat the test fluid contained in the microchannel and measure its temperature accurately. Alternatively, as shown in FIG. 1B, in the second arrangement, the heater wire 20 and the sensor wire 22 are placed on the opposite side of the microchannels, so that the sensor wire 22 is closer to the microchannel, to be able to measure the temperature of the test fluid contained therein more accurately.

However, in this arrangement, the additional insulation layer 26 utilized could incur additional production cost.

SUMMARY OF THE INVENTION

In view of the above-mentioned problems and shortcomings of the prior art, the object of the invention is to provide a microfluidic chip, which can be utilized to overcome the problems and the shortcomings of the prior art and fulfill the actual requirement of the related industry.

Therefore, to achieve the above-mentioned objective, the invention provides a microfluidic chip, which can be utilized in the biochemical reaction process required such that the localized temperature control of the microchannel is achieved for controlling the temperature of the biochemical cultivation fluid utilized in the cell cultivation. In this connection, the microfluidic chip is mainly composed of a main body made of transparent material and an electrode layer, wherein the microchannel is provided in the main body, so that the test fluid can be made to flow in the microchannel of the main body while the electrode layer is provided with the heater wire and the sensor wire disposed on one side and in the vicinity of the microchannel respectively, thus supplying heat energy to the test fluid contained therein and measuring its temperature, as such fully taking advantage of its large surface area, and ensuring quick reaction to the temperature variations of the heat source, thus achieving the rapid rise and fall of the temperature of the microfluidic chip, and realizing the purpose of multiplying the sample body in a very short time. In addition, through the application of the invention, the temperature control process can be achieved without utilizing the insulation layer, so that the production cost can be reduced significantly, meanwhile, the precise temperature control of the microfluidic chip can also be realized.

Further scope of the applicability of the present invention will become apparent from the detailed description given hereinafter. However, it should be understood that the detailed description and specific examples, while indicating preferred embodiments of the present invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given below, which is for illustration only and thus is not limitative of the present invention, wherein.

DETAILED DESCRIPTION OF THE INVENTION

The purpose, construction, features, and functions of the present invention can be appreciated and understood more thoroughly through the following detailed description with reference to the attached drawings.

Figure 2A:
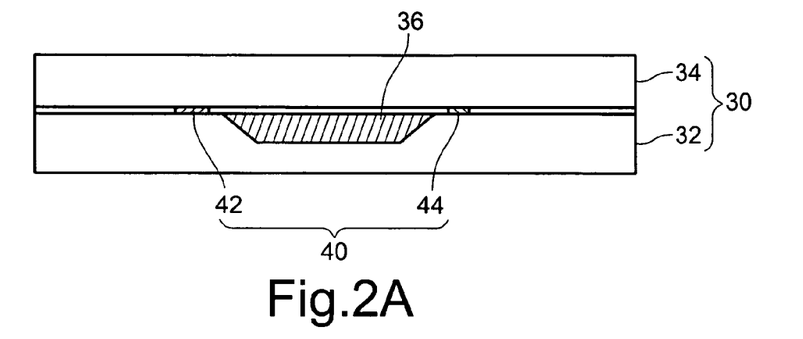
FIGS. 2A and 2B are the schematic diagrams of the cross section view and plane view respectively of the microfluidic chip according to the first embodiment of the invention.
Figure 2B:
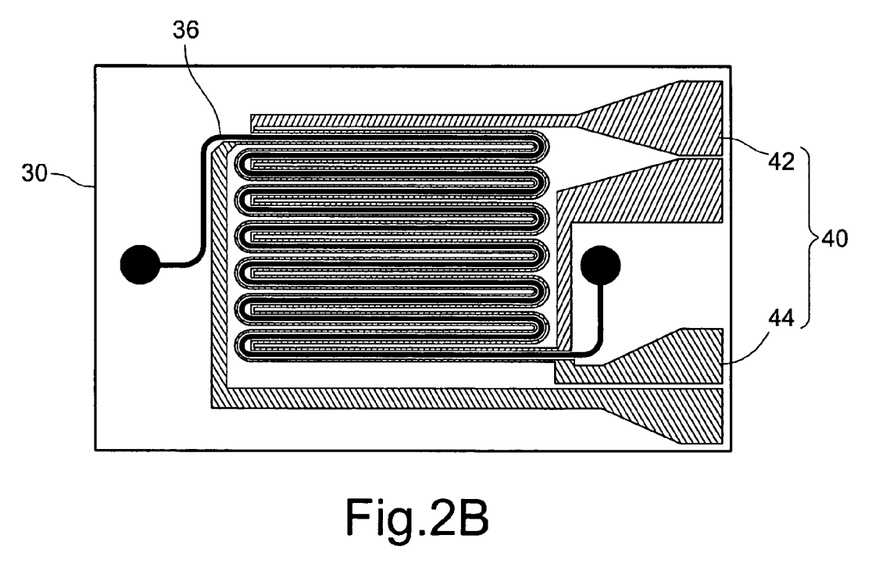

Firstly, refer to FIGS. 2A and 2B for the schematic diagrams of the cross section view and plane view respectively of the microfluidic chip according to the first embodiment of the invention. Said microfluidic chip can be utilized in the chain reactions of the growth of the poly-enzyme mainly including: a main body 30 and an electrode layer 40. The main body 30 includes a first substrate 32 and a second substrate 34. A serpentine-winding shape microchannel 36 is provided on the first substrate 32, which can be used to contain the test fluid flowing therein for the experimental analysis of the cell or the sample body, by taking advantage of its feature of miniature size and fast reaction speed. For the requirement of optical observation, the main body 30 is made of glass material, having a good light transmission capability, as such facilitating the optical observation of the processing and the operation of the test fluid.

In practice, the electrode layer 40 is made of metal having a melting point higher than 800° C., such as titanium (Ti), platinum (Pt), chromium (Cr) and gold (Au). The electrode layer 40 is provided with a heater wire 42 and a sensor wire 44. The heater wire 42 is disposed along one side of the microchannel 36 and is used to heat the test fluid, while the sensor wire 44 is disposed along the other side of the microchannel 36, and is used to sense the temperature of the test fluid.

In the design of the microfluidic chip of the invention, the heater wire 42 and the sensor 44 are placed on either side of the microchannel 36 respectively, so that the temperature variation of the test fluid contained in the microchannel 36 is thus able to respond quickly to the heat from the heater wire 42, while the temperature measured by the sensor wire 44 is able to get close to the actual temperature of the test fluid contained in the microchannel 36. Thus the unique and special design of the invention of sandwiching the microchannel 36 with the heater wire 42 and the sensor wire 44 is utilized to avoid the direct contact of the test fluid with the heater wire 42 and the sensor wire 44 without the necessity of using the insulation layer, so that the production cost can be reduced significantly.

Now, we are going to describe the design and the structure of the microfluidic chip according to the first embodiment of the invention. Firstly, a microchannel 36 is formed on the first substrate 32 by the wet etching, and an electrode layer 40 is made by sputtering the metal thin film on the second substrate 34 by the sputtering process. Then the first substrate 32 and the second substrate 34, both made of glass material, are bonded together through the thermal fusion bonding method, thus realizing the microfluidic chip by disposing the electrode layer 40 and microchannel 36 in the main body 30, made of glass material. Subsequently, after certain holes are bored on one side of the first substrate 32 and the second substrate 34, said chip is connected to a planar acrylic plate, a soft tube, an electric power source connection wire and the terminal of the fluid driving power source. As such, it can be utilized to implement the multiplication and reproduction of the DNA through repeatedly breaking and connecting the hydrogen bonds of the DNA by the temperature rising and falling of the test fluid in the microchannel of the microfluidic chip, thus facilitating the subsequent tests of the sample body.

Alternatively, in practice, the electrode layer 40 of the present embodiment may also be formed on the first substrate 34, the microchannel 36 may also be made by dry etching or through laser processing. Besides, the microchannel 36 is not limited to a serpentine-winding shape, for example, it may be realized in a linear manner. In addition, the bonding of the first substrate 32 and the second substrate 34 may be achieved through the bonding of the chemical bonds or some specific physical process.

Subsequently, the steps of making the microchannel 36 of the microfluidic chip are described in detail as follows:

Firstly, after executing the wet etching process by the hard mask made of gold and chromium, the first substrate 32 is subjected to the process of exposing the photo resistance disposed thereon to light and the subsequent developing and fixing processes; then it is immersed in the etching solution of potassium indium (KI) and chromium, to remove the metals on the structure desired to be etched, then the first substrate 32 is dipped into the hydrofluoric acid solution to remove gradually the glass material not protected by the photo resistance. As such, the microchannel 36 having the desired etching depth is made according to the time of dipping the substrate 32 into the hydrofluoric acid solution, based on the calculated etching speed. Finally, the photo resistance and the metals gold and chromium of the remaining hard mask are removed, thus realizing the fully transparent first substrate 32, having the microchannel 36.

Then, the above-mentioned first substrate 32 and the second substrate 34 having the electrode layer 40 are bonded together through the thermal fusion bonding method, thus realizing the superior bonding structure. According to the scanning image of the cross section of the microchannel 36 made by the scanning electronic microscope, there appears almost no slit in the connection between the second substrate 34 and the microchannel 36. Furthermore, the signals transmitted through the bonded electrode layer 40 are just as normal as before the bonding, and they do not show any signs of being interrupted, due to the presence of the microchannel 36. From the contents of Table 1 it is evident that the values of the electric resistance of the electrode layer 40 change slightly after the thermal fusion bonding. This is due to the fact that the lattice structure of the atoms formation of the electrode layer 40 realigns itself during the thermal fusion bonding process, so that the difference between the first substrate 32 and the second substrate 34 is reduced, thus they are more suitable for use in temperature sensing.

Figure 3A:
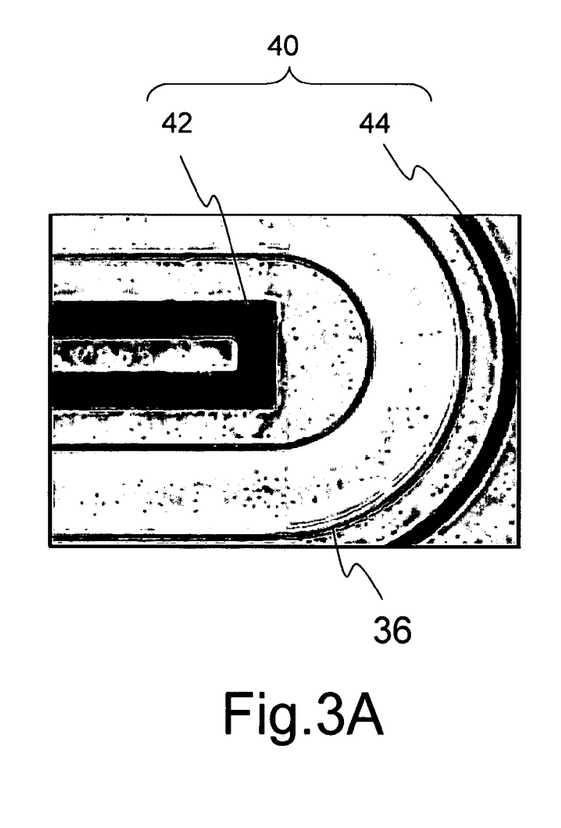
FIGS. 3A and 3B are the detailed optical photo and local cross section SEM photo respectively of the microfluidic chip according to the first embodiment of the invention.
Figure 3B:
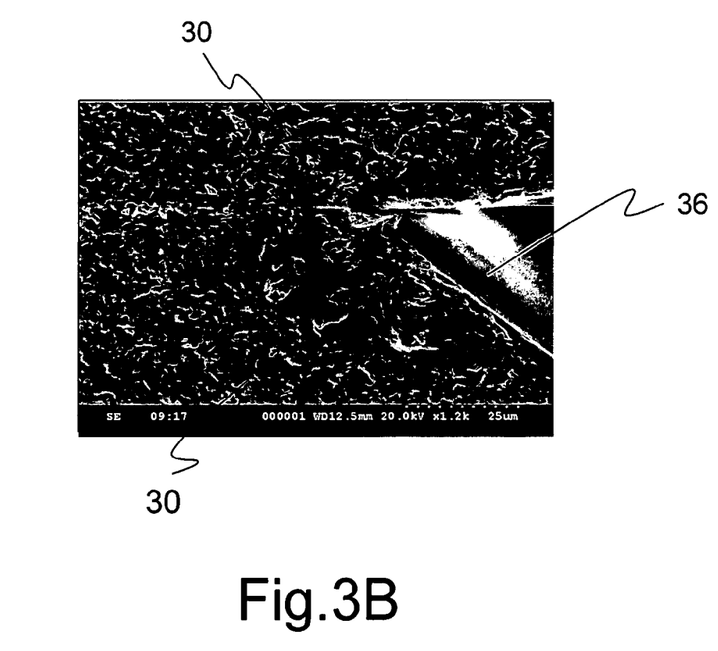

For further description of the structure of bonding the first substrate 32 to the second substrate 34 through the thermal fusion bonding according to the first embodiment of the invention, refer to FIGS. 3A and 3B. As shown in FIGS. 3A and 3B, it shows the detailed optical photograph and the localized portion cross section SEM photograph of the microchannel-electrode-on-chip structure respectively as taken by the scanning electronic microscope according to the first embodiment of the invention. In FIG. 3A, it is shown that the electrode layer 40 does not indicate any dislocation after the thermal fusion bonding. The heater wire 42 and the sensor wire 44 are disposed on either side of the microchannel 36, and they are in good bonding relations with the glass main body 30. From FIG. 3B, it is known that the bonding is excellent; there are almost no slits between the microchannel 36 and the glass main body 30.

Figure 4:
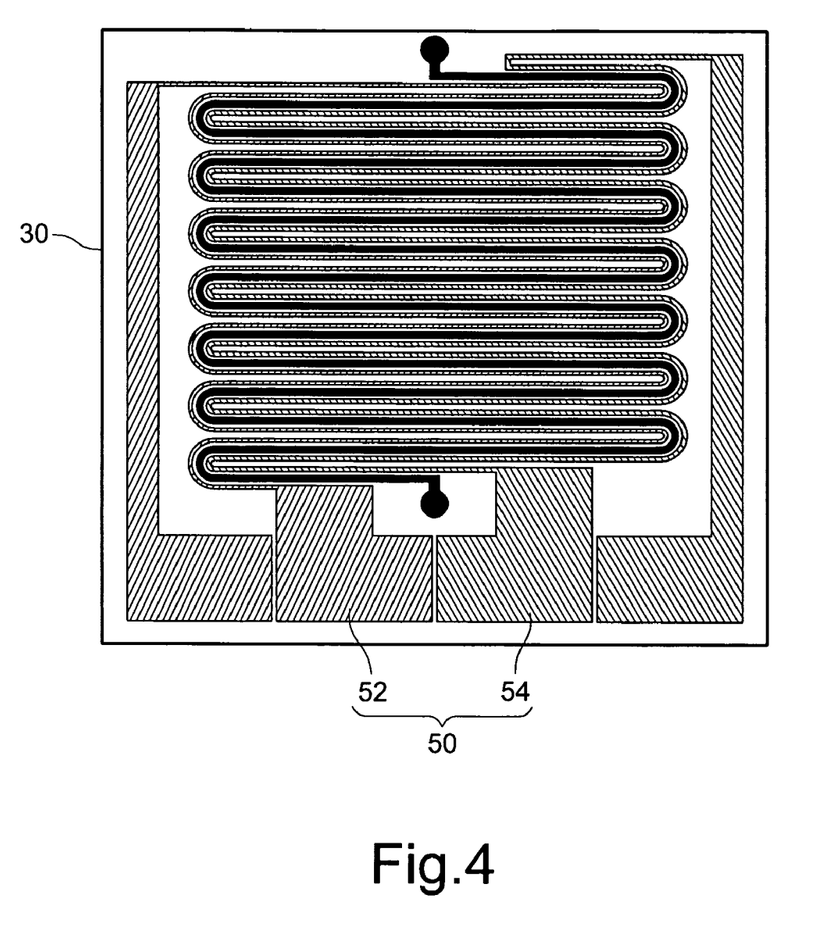
FIG. 4 is a schematic diagram of the plane view of the microfluidic chip according to the second embodiment of the invention.

In addition, in order to increase the product utilization rate of a single wafer to reduce the production cost, the 6 microchannel-electrode-on-chip structures, originally designed to be placed on a 4-inch wafer, are increased to 12 the microchannel-electrode-on-chip structures. As shown in FIG. 4, it illustrates the schematic diagram of the plane view of the microchannel-electrode-on-chip structure according to the second embodiment of the invention. In order to obtain the optimal design, the width and the spacing of the electrode layer 50 (including the heater wire 52 and the sensor wire 54) are changed respectively, to realize the optimized temperature variations.

Moreover, in order to fully understand the effect of utilizing the various metals as the material of the electrode layer, experiments are conducted for varying the metal utilized for the electrode layer of the microfluidic chip. So chromium (Cr), gold (Au), titanium (Ti), and platinum (Pt) are sputtered respectively on the glass substrate, then the values of the electrical resistance corresponding to the various line width arrangements are compared. As shown in Table 2, the larger the heater wire width, the smaller its electrical resistance value, and the speed of the temperature increase is faster when it is utilized as a heater wire. In Table 2, W is used to indicate the width of the heater wire, and S is used to indicate the spacing between the heater wire and the sensor wire. As it is evident from Table 2 that concerning the same current range, the larger the heater wire width, the smaller its electric resistance, the speed of the temperature increase is faster, yet the area available for the microchannel is reduced. To the contrary, the smaller the heater wire width the larger its electric resistance, so that the speed of the temperature increase is slower, however, the area available for the microchannel is increased. Experiments are conducted for comparing the speed of the temperature increases versus the heater wire width, to achieve the optimized the microfluidic chip.

TABLE 1

|   | heater wire (before bonding) | sensor wire (after bonding) | heater wire (before bonding) | sensor wire (after bonding) |
|---|---|---|---|---|
| I | 266 Ω | 377 Ω | 138 Ω | 207 Ω |
| II | 333 Ω | 1229 Ω | 150 Ω | 614 Ω |
| III | 308 Ω | 1134 Ω | 159 Ω | 648 Ω |
| IV | 266 Ω | 372 Ω | 140 Ω | 209 Ω |
| V | 334 Ω | 1233 Ω | 149 Ω | 610 Ω |
| VI | 310 Ω | 1141 Ω | 162 Ω | 653 Ω |

TABLE 2

| W | 200 μm | 200 μm | 300 μm | 400 μm | 450 μm | 500 μm | 500 μm | 600 μm | 800 μm |
|---|---|---|---|---|---|---|---|---|---|
| S | 600 μm | 500 μm | 500 μm | 400 μm | 400 μm | 350 μm | 300 μm | 200 μm | 50 μm |
| Ti, Pt | 1730 Ω | 1730 Ω | 1230 Ω | 880 Ω | 830 Ω | 610 Ω | 910 Ω | 580 Ω | 410 Ω |
| Cr, Au | 468 Ω | 463 Ω | 280 Ω | 170 Ω | 191 Ω | 155 Ω | 192 Ω | 124 Ω | 111 Ω |

Figure 5A:
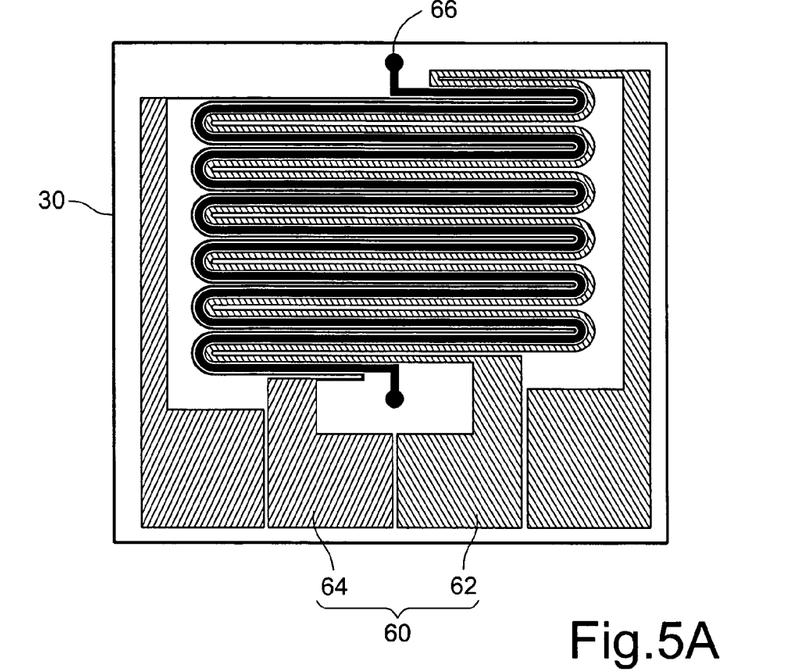
FIGS. 5A and 5B are the schematic diagrams of the plane views of the microfluidic chip according to the third embodiment of the invention.
Figure 5B:
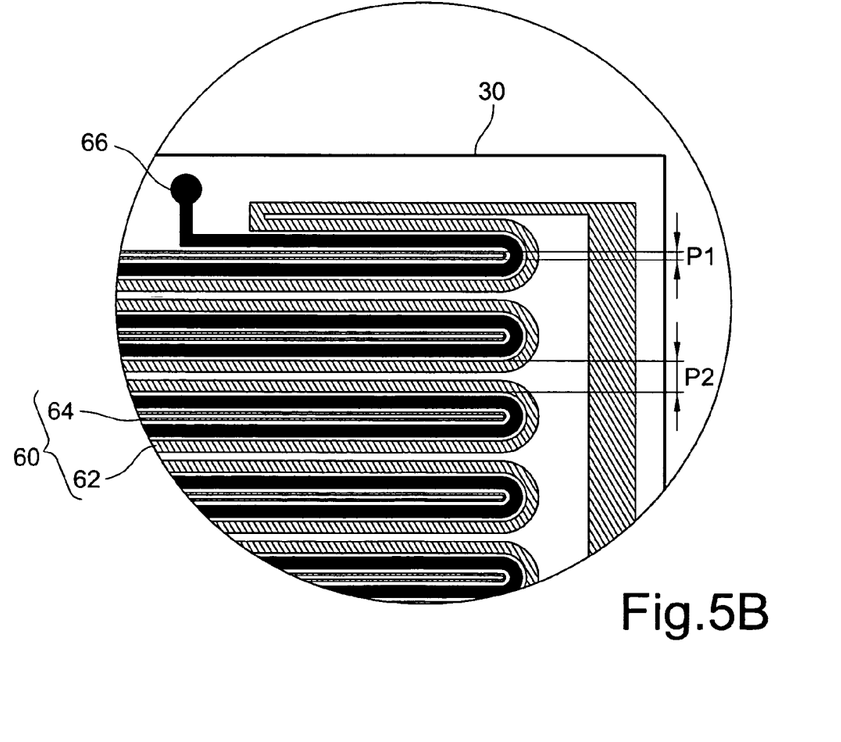

Furthermore, refer to FIGS. 5A and 5B for the schematic diagrams of the plane views of the microfluidic chip according to the third embodiment of the invention, which is an improvement of the second embodiment. In this embodiment, the spacings between the electrode layers 60 (including the heater wire 62 and the sensor wire 64) are varied and different, which is used to achieve the optimized utilization of the space in said chip, by reducing the winding spacing P1 between the sensor wires 64 and increasing the winding spacing P2 between the heat wire 62, as such obtaining at the same time the raise of the temperature variation efficiency, the increase of the temperature measuring sensitivity, and the augmentation of the size of the microchannel 66, thus achieving the optimized control of the temperature feedback of the microfluidic chip.

In the third embodiment of the invention, the heater wire and the sensor wire are disposed respectively along the main body on either side of the microchannel.

Figure 6A:
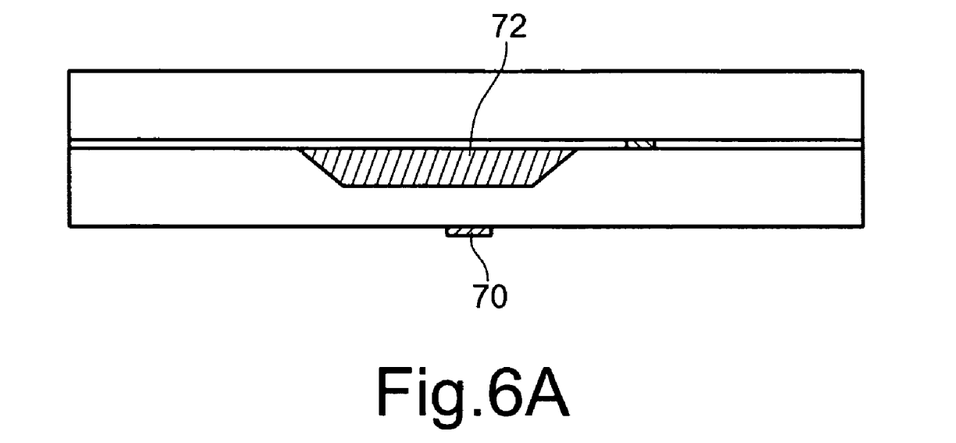
FIGS. 6A and 6B are the schematic diagrams of the cross section views of the microfluidic chip according to the fourth and the fifth embodiments of the invention respectively.
Figure 6B:
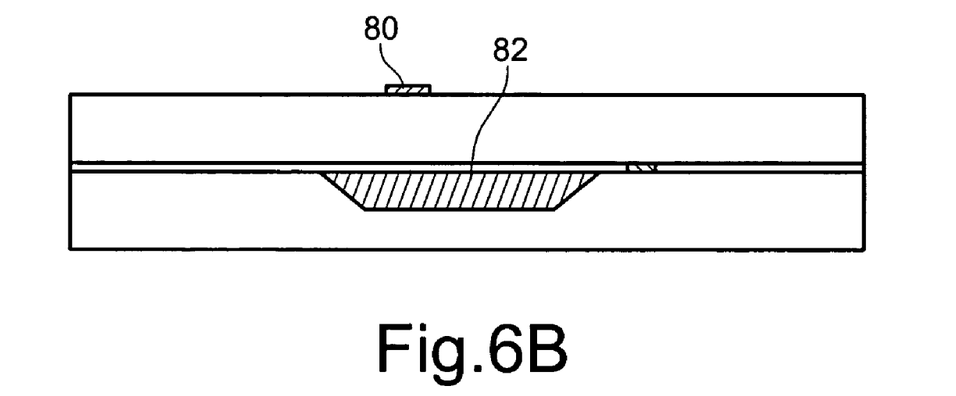

However, in practical applications, other designs are possible, as long as the heater wire is disposed in the vicinity of the microchannel. For example, as shown in FIG. 6A, the heater wire 70 is provided at the backside of the microchannel 72, thus constituting the fourth embodiment of the invention. In addition, as shown in FIG. 6B, the heater wire 80 is provided at the opposite side of the microchannel 82, thus constituting the fifth embodiment of the invention.

Besides, one-sided or two-sided of the main body may be made of the transparent material selected from the group including of glass, rock crystals, plastics, resins, photo resists, transparent ceramics and synthetic materials thereof. The one-sided transparent main body limits the observation scope, and the two-sided transparent main body is provided for the front and the back observation.

Summing up the above, the microfluidic chip of the invention has the following advantages: firstly, the transparent material is utilized as the material of the main body, thus facilitating the subsequent examinations utilizing optical observations following the multiplication and augmentation of the sample body. Secondly, due to the fact that the main body made of glass material may be cleaned and washed and used repeatedly. Furthermore, it is made of hydrophilic material, thus the capacity required for the driving power source of the test fluid can be reduced. Thirdly, in cooperation with the previous process flow, the test fluid containing the sample body can be made entirely in the microchannel, thus facilitating the automation of the production process, and as such reducing the space required for the biochemical reactions, raising the speed of the biochemical reactions, and reducing pollution of the environment. And finally and most importantly, the electrode layer can be disposed closer to the microchannel without requiring the protection of the insulation layer, thus reducing the production cost.

Knowing the invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A microfluidic chip, comprising:
 a main body, which is made of a transparent material and is provided with a serpentine-winding shape microchannel for containing a fluid flowing therein; and
 an electrode layer, provided with a heater wire around one side of the microchannel and a sensor wire around the other side of the microchannel, said heater wire being disposed around one side of said microchannel of said main body, said sensor wire being disposed on the other side of said microchannel of said main body, said heater wire being used to heat said fluid in said microchannel, and the temperature of said fluid being sensed by said sensor wire, wherein the length of the heater wire and the length of the sensor wire are substantially coextensive with the length of the microchannel, said heater wire and said sensor wire extending beyond the length of the microchannel to the edge of the main body.

2. The micro fluidic chip of claim 1, wherein said transparent material is a silicon base material.

3. The microfluidic chip of claim 2, wherein said silicon base material is selected from a group consisting of glass, rock crystals, and synthetic materials thereof.

4. The microfluidic chip of claim 1, wherein said transparent material is selected from a group consisting of a transparent ceramics and synthetic materials thereof.

5. The microfluidic chip of claim 1, wherein said transparent material is a polymer.

6. The microfluidic chip of claim 5, wherein said polymer is selected from a group consisting of plastics, resins, photo resists, and synthetic materials thereof.

7. The microfluidic chip of claim 1, wherein said heater wire and said sensor wire are disposed along the either side of said microchannel of said main body respectively.

8. The microfluidic chip of claim 1, wherein said heater wire is disposed at one side of said main body and at the opposite side of said microchannel.

9. The microfluidic chip of claim 1, wherein said heater wire is disposed at one side of said main body and at the back side of said microchannel.

10. The microfluidic chip of claim 1, wherein said main body is composed of a first substrate and a second substrate.

11. The microfluidic chip of claim 10, wherein said microchannel is formed on said first substrate.

12. The microfluidic chip of claim 10, wherein said microchannel is formed by a method selected from one group consisted of dry etching, wet etching, and laser processing.

13. The microfluidic chip of claim 10, wherein said electrode layer is formed on said second substrate by sputtering.

14. The microfluidic chip of claim 10, wherein said electrode layer is formed on both sides of said microchannel of said first substrate by coating.

15. The microfluidic chip of claim 10, wherein said first substrate and said second substrate is bonded together by thermal fusion bonding.

16. The microfluidic chip of claim 10, wherein said first substrate and said second substrate is bonded together by the chemical bonds bonding method or the physical bonding method.

17. The microfluidic chip of claim 1, wherein a winding spacing between said heater wire is greater than a winding spacing between said sensor wire.

18. The microfluidic chip of claim 1, wherein said electrode layer is made of a metal having melting point greater than 800° C.

19. The microfluidic chip of claim 18 wherein said electrode layer is selected from one group consisted of the group of titanium, platinum, chromium and gold.

* * * * *